United States Patent [19]

Riley et al.

[11] Patent Number: 4,965,402
[45] Date of Patent: Oct. 23, 1990

[54] PROCESS FOR PRODUCING N-PHOSPHONOMETHYLGLYCINE

[75] Inventors: Dennis P. Riley, Chesterfield; Willie J. Rivers, Jr., University City, both of Mo.

[73] Assignee: Monsanto Company, St. Louis, Mo.

[21] Appl. No.: 311,786

[22] Filed: Feb. 17, 1989

Related U.S. Application Data

[62] Division of Ser. No. 112,594, Oct. 26, 1987, Pat. No. 4,853,159.

[51] Int. Cl.$^5$ ............................................. C07F 9/38
[52] U.S. Cl. ............................................. 562/17
[58] Field of Search ........................................ 562/17

[56] References Cited

U.S. PATENT DOCUMENTS

| | | | |
|---|---|---|---|
| 3,969,398 | 7/1976 | Hershman | 260/502.5 F |
| 4,147,719 | 4/1979 | Franz | 260/502.5 F |
| 4,442,041 | 4/1984 | Subramanian | 260/502.5 F |
| 4,579,689 | 4/1986 | Hershman et al. | 260/502.5 F |
| 4,582,650 | 4/1986 | Felthouse | 260/502.5 F |
| 4,696,772 | 9/1987 | Chou | 260/502.5 F |

FOREIGN PATENT DOCUMENTS

| | | | |
|---|---|---|---|
| 125363 | 11/1984 | European Pat. Off. | 260/502.5 F |
| 187347 | 2/1984 | Hungary . | |
| 2049697 | 12/1980 | United Kingdom | 260/502.5 F |

OTHER PUBLICATIONS

Motekaitis et al. (I), Can. J. Chem. 58, 1999 (1980).
Motekaitis et al (II)., Can. J. Chem. 60, 1207 (1982).

*Primary Examiner*—J. E. Evans
*Attorney, Agent, or Firm*—Linda L. Lewis; Frank D. Shearin

[57] ABSTRACT

A process for producing N-phosphonomethylglycine by the oxidation of N-phosphonomethyliminodiacetic acid using a molecular oxygen-containing gas in the presence of a transition metal catalyst.

7 Claims, No Drawings

PROCESS FOR PRODUCING N-PHOSPHONOMETHYLGLYCINE

This application is a division of application 07/112,594 filed Oct. 26, 1987, now U.S. Pat. No. 4,853,159 issued Aug. 1, 1989.

FIELD OF THE INVENTION

This invention relates to a process for producing N-phosphonomethylglycine by the oxidation of N-phosphonomethyliminodiacetic acid using transition metal catalysts. More particularly, this invention relates to a reaction using molecular oxygen and a transition metal salt catalyst.

SUMMARY OF RELATED ART

It is known in the art that N-phosphonomethylglycine can be produced by oxidizing N-phosphonomethyliminodiacetic acid using various oxidizing methods. U.S. Pat. No. 3,950,402 discloses a method wherein N-phosphonomethyliminodiacetic acid is oxidized to N-phosphonomethylglycine in aqueous media using a free oxygen-containing gas and a heterogeneous noble metal-based catalyst such as palladium, platinum or rhodium. U.S. Pat. No. 3,954,848 discloses the oxidation of N-phosphonomethyliminodiacetic acid with hydrogen peroxide and an acid such as sulfuric or acetic acid. U.S. Pat. No. 3,969,398 discloses the oxidation of N-phosphonomethyliminodiacetic acid using molecular oxygen and a heterogeneous activated carbon catalyst. Hungarian Patent Application No. 011706 discloses the oxidation of N-phosphonomethyliminodiacetic acid with peroxide in the presence of metals or metal compounds. R. J. Motekaitis, A. E. Martell, D. Hayes and W. W. Frenier, Can. J. Chem., 58, 1999 (1980) disclose the iron(III) or copper(II) catalysed oxidative dealkylation of ethylene diaminetetracetic acid (EDTA) and nitrilotriacetic acid (NTA), both of which have iminodiacetic acid groups. R. J. Moteakitis, X. B. Cox, III, P. Taylor, A. E. Martell, B. Miles and T. J. Tvedt, Can. J. Chem., 60, 1207 (1982) disclose that certain metal ions, such as Ca(II), Mg(II), Fe(II), Zn(11) and Ni(II) chelate with EDTA and stabilize against oxidation, thereby reducing the rate of oxidative dealkylation.

SUMMARY OF THE INVENTION

The present invention involves a process for the production of N-phosphonomethylglycine comprising contacting N-phosphonomethyliminodiacetic acid with a molecular oxygen-containing gas in the presence of a transition metal catalyst.

DETAILED DESCRIPTION OF THE INVENTION

The process of this invention involves contacting N-phosphonomethyliminodiacetic acid with a transition metal catalyst in a mixture or solution. This mixture or solution is contacted with a molecular oxygen-containing gas while heating the reaction mass to a temperature sufficiently elevated to initiate and sustain the oxidation reaction of N-phosphonomethyliminodiacetic acid to produce N-phosphonomethylglycine.

The transition metal catalyst of the present invention can be any one or more of several transition metal compounds such as manganese, cobalt, iron, nickel, chromium, ruthenium, aluminum, molybdenum, vanadium and cerium. The catalysts can be in the form of salts such as manganese salts, e.g., manganese acetate, manganese sulfate; complexes such as manganese(II)bis(acetylacetonate) $(Mn(II)(acac)_2)$; cobalt salts such as Co(II)(SO$_4$), Co(II)(acetylacetonate), CoCl$_2$, CoBr$_2$, Co(NO$_3$)$_2$ and cobalt acetate; cerium salts such as $(NH_4)_4Ce(SO_4)$ and $(NH_4)_2Ce(NO_3)_6$, iron salts such as $(NH_4)_2Fe(SO_4)_2$, iron(III)(dicyano)-(bisphenanthroline)$_2$-(tetrafluoro)borate salt and $K_3Fe(CN)_6$, and other metal salts such as $NiBr_2$, $CrCl_3$, $RuCl_2(Me_2SO)$, $RuBr_3$, $Al(NO_3)_3$, $K_4Mo(CN)_8$, $VO(acetylacetonate)_2$ and $VOSO_4$. The catalyst can be added to the N-phosphonomethyliminodiacetic acid in the salt form, or a salt may be generated in situ by the addition of a source of a transition metal ion such as $MnO_2$ which dissolves in the reaction medium. The Mn(III)-chloro(phthalocyaninato), however, is not catalytic, possibly because the phthalocyanine ligand covalently bonds to the Mn(111) and therefore inhibits the formation of N-phosphonomethyliminodiacetic acid/ manganese complex in solution.

Manganese salts such as Mn(II), Mn(III) or Mn(IV) salts can be used individually, however, the reaction displays a delayed reaction initiation time (initiation period), e.g., there is a delay before any N-phosphonomethylglycine is produced. When a mixture of Mn(II) and Mn(III) salts are used as a catalyst system, the initiation is diminished or eliminated. A preferred manganese salt catalyst is a mixture of Mn(II) and Mn(III) salts in the range of 1:10 to 10:1 mole ratio of the Mn ions. A most preferred manganese catalyst salt is a 1:1 mole ratio of Mn(II) and Mn(III) ions in the form of manganese acetate salts. A preferred cobalt catalyst is a Co(II) salt such as Co(II)(SO$_4$), Co(II)Cl$_2$, Co(II)Br$_2$, Co(II)(OH)$_2$ and Co(II)acetate.

The concentration of the transition metal catalyst in the reaction solution can vary widely, in the range of 0.1M to 0.0001M total metal ion concentration. For manganese, the reaction appears to have a first order dependency on the catalyst concentration, e.g., the reaction rate increases linearly as the catalyst concentration increases. The preferred concentration is in the range of about 0.01M to about 0.001M, which gives a suitably fast rate of reaction that can be easily controlled and favors selectivity to N-phosphonomethylglycine.

The reaction temperature is sufficient to initiate and sustain the oxidation reaction, in the range of about 25° C to 150° C. In general, as the reaction temperature increases, the reaction rate increases. To achieve an easily controlled reaction rate and favor selectivity to N-phosphonomethylglycine, a preferred temperature range is about 50° C. to 120° C. and a most preferred is in the range of about 70° C. to 100° C. If a temperature of above about 100° C. is used, pressure will have to be maintained on the system to maintain a liquid phase.

The pressure at which this process is conducted can vary over a wide range. The range can vary from about atmospheric (101 kPa) to about 3000 psig (20700 kPa). A preferred range is about 30 psig (200 kPa) to about 1000 psig (about 6900 kPa). A most preferred range is from about 150 psig (about 1000 kPa) to 600 psig (about 4140 kPa).

The oxygen concentration, as designated by the partial pressure of oxygen (PO$_2$), in the reaction affects the reaction rate and the selectivity to the desired product, N-phosphonomethylglycine. As the PO$_2$ increases, the reaction rate generally increases and the selectivity to N-phosphonomethylglycine increases. The $PO_2$ can be increased by increasing the overall reaction pressure, or by increasing the molecular oxygen concentration in the molecular oxygen-containing gas. The $PO_2$ can vary widely, in the range of from 1 psig (6.9 kPa) to 3000 psig (20700 kPa). A preferred range is from 30 psig (207 kPa) to 1000 psig (6900 kPa).

The term "molecular oxygen-containing gas" means molecular oxygen gas or any gaseous mixture containing molecular oxygen with one or more diluents which are non-reactive with the oxygen or with the reactant or product under the conditions of reaction. Examples of such diluent gases are air, helium, argon, nitrogen, or other inert gas, or oxygen-hydrocarbon mixtures. A preferred molecular oxygen is undiluted oxygen gas.

The manner in which the solution or mixture of the N-phosphonomethyliminodiacetic acid is contacted with molecular oxygen can vary greatly. For example, the N-phosphonomethyliminodiacetic acid solution or mixture can be placed in a closed container with some free space containing molecular oxygen and shaken vigorously or agitated by stirring. Alternatively, the molecular oxygen can be continuously bubbled through the solution or mixture containing the transition metal catalyst using a straight tube or a tube with a fritted diffuser attached to it. The process of this invention only requires actively contacting the molecular oxygen-containing gas with the aqueous solution or mixture of the N-phosphonomethyliminodiacetic acid containing a transition metal catalyst.

The initial pH (pHi) of the reaction affects the reaction rate and the selectivity to N-phosphonomethylglycine. For example, with manganese, as the initial pH increases, the reaction rate increases, but the selectivity to N-phosphonomethylglycine decreases. The pHi of the reaction can vary widely, in the range of about 0.1 to about 7. A preferred range is about 1 to about 3 with manganese and about 0.1 to 3 with cobalt. A most preferred pH is the unadjusted pH of N-phosphonomethyliminodiacetic acid in a water solution which varies with the N-phosphonomethyliminodiacetic acid concentration and the reaction temperature.

The oxidation reaction can take place in a solution or slurry. For a solution, the initial concentration of the N-phosphonomethyliminodiacetic acid in the reaction mass is a function of the solubility of the N-phosphonomethyliminodiacetic acid in the solvent at both the desired reaction temperature and the pHi of the solution. As the solvent temperature and pH changes, the solubility of the N-phosphonomethyliminodiacetic acid changes. A preferred initial concentration of the N-phosphonomethyliminodiacetic acid is a saturated slurry containing a solvent system at reaction conditions, which maximize the yield of N-phosphonomethylglycine in the reaction mass. A preferred concentration of N-phosphonomethyliminodiacetic acid is in the range of about 1 to 50 wt.%. It is, of course, possible to employ very dilute solutions of N-phosphonomethyliminodiacetic acid, or slurries and mixtures.

The reaction is typically carried out in an aqueous solvent. The term aqueous solvent means solutions containing at least about 50 weight % water. The preferred aqueous solvent is distilled, deionized water.

The following examples are for illustration purposes only and are not intended to limit the scope of the claimed invention.

EXAMPLES

A series of runs were made to oxidize N-phosphonomethyliminodiacetic acid to N-phosphonomethylglycine. The reactions were conducted in a modified Fisher-Porter glass pressure apparatus or an Engineer Autoclave 300 ml pressure reactor in which a stirrer was installed in the head, as were three additional valved ports that were used as a sample port, a gas inlet, and a purged gas outlet. The stirrer maintained sufficient agitation to afford thorough gas-liquid mixing. The temperature was controlled by immersing the reactor in a constant temperature oil bath. The indicated amount of transition metal catalyst was dissolved or suspended in a distilled, deionized water solution containing the indicated amount of N-phosphonomethyliminodiacetic acid. The reactor was sealed and heated to the indicated reaction temperature, then pressurized to the indicated $PO_2$ with oxygen gas. Agitation was initiated.

The selectivity (mole%) to N-phosphonomethylglycine was determined by dividing the moles of N-phosphonomethylglycine produced by the total moles of N-phosphonomethyliminodiacetic acid consumed and multiplying by 100. The yield (mole%) of N-phosphonomethylglycine was determined by dividing the moles of N-phosphonomethylglycine produced by the total moles of starting M-phosphonomethyliminodiacetic acid an multiplying by 100.

Examples 1 through 8

Examples 1 through 8, shown in Table 1, show the effect of varying the manganese catalyst concentration. In examples 1-4 the reaction temperature was 90° C., the $PO_2$ was 100 psig (690 kPa), the initial N-phosphonomethyliminodiacetic acid concentration was 0.1M. The catalyst was a mixture of Mn(II) and Mn(III) acetate salts in a 1:1 mole ratio of Mn(II) and Mn(III). Examples 5–8 were run at the same conditions as 1–4, except that the $PO_2$ was 450 psig (3100 kPa) and the reaction temperature was 80° C. and the catalyst was Mn(II) acetate.

TABLE 1

| | Effect of Varying Catalyst Concentration | | | |
|---|---|---|---|---|
| Examples | Selectivity to N-phosphonomethylglycine (Mole %) | Manganese Concentration (M) | Initial Reaction Rate (Velocity, M/hr) | Yield of N-Phosphonomethyl glycine (Mole %) at indicated time (h) |
| 1 | 58 | 0.008 | 0.23 | 53 (6) |
| 2 | 82 | 0.004 | 0.10 | 75 (6) |
| 3 | 84 | 0.002 | 0.05 | 18 (1¼) |
| 4 | 63 | 0.001 | 0.016 | 45 (6) |
| 5 | 83 | 0.02 | 0.30 | 83 (⅔) |
| 6 | 83 | 0.0067 | 0.10 | 81 (½) |
| 7 | 70 | 0.004 | 0.07 | 68 (6) |
| 8 | 74 | 0.002 | 0.034 | 68 (6) |

The data indicated that the reaction rate increases with the catalyst concentration. There appeared to be a first-order dependence of the reaction rate on the catalyst concentration.

Examples 9 through 13

Examples 9 through 13, shown in Table 2, illustrate the effect of initial pH on the reaction rate and selectivity to N-phosphonomethylglycine for a manganese catalyst. The reaction temperature was 80° C., the PO$_2$ was 100 psig (690 kPa), the initial N-phosphonomethyliminodiacetic acid concentration was 0.1M, the reaction times are indicated and the manganese ion concentration was 0.004M. The mixture of manganese salts was the same as used in Example 1. The initial pH was adjusted using sodium hydroxide or sulfuric acid solutions. The data indicate that as the initial pH increases, the reaction rate increases, but the selectivity to N-phosphonomethylglycine decreases.

TABLE 2

Effect of Varying Initial pH

| Example | Initial pH | Initial Reaction Rate (M/h) | Yield of N-phosphonomethyl glycine (Mole %) at indicated time (h) | Selectivity to N-phosphonomethyl glycine (Mole %)(h) |
|---|---|---|---|---|
| 9 | 1.20 | 0.0103 | 31 (6) | 49 (6) |
| 10 | 1.35 | 0.015 | 56 (5) | 66 (5) |
| 11 | 1.80 | 0.11 | 41 (2½) | 44 (2½) |
| 12 | 2.30 | 0.14 | 36 (2½) | 37 (2½) |
| 13 | 3.50 | 0.32 | 39 (39) | 41 (½) |

Examples 14 through 16

Examples 14 through 16, shown in Table 3, illustrate the effect of reaction temperature on reaction rates and selectivity to N-phosphonomethyl glycine for a manganese catalyst. The PO$_2$ was 450 psig, the initial N-phosphonomethyliminodiacetic acid concentration was 0.1M and the manganese ion concentration was 0.067M. The form of the manganese salt was Mn(II)SO$_4$ and the pH was the unadjusted pH of the acid solution.

The data indicated that as the reaction temperature increased, the reaction rate increased.

TABLE 3

Effect of Varying Temperature

| Example | Temperature (°C.) | Initial Reaction Rate (M/hr) | Selectivity to N-phosphonomethyl glycine (Mole %) at indicated time (h) | Yield of N-phosphonomethyl glycine (Mole %) at indicated time (h) |
|---|---|---|---|---|
| 14 | 70 | 0.035 | 77 (5) | 75 (5) |
| 15 | 80 | 0.093 | 83 (1½) | 81 (1½) |
| 16 | 90 | 0.310 | 80 (½) | 77 (½) |

Examples 17 through 22

Examples 17 through 22, shown in Table 4, illustrate the effect of PO$_2$ on selectivity to N-phosphonomethylglycine for a manganese catalyst. The reaction temperature was 80° C., the initial N-phosphonomethyliminodiacetic acid concentration was 0.1, the reaction time was as indicated which allowed for almost complete conversion of the N-phosphonomethyliminodiacetic acid, and the manganese ion concentration was 0.006 M. The form of the manganese salt was Mn(II)SO$_4$ and the pHi was the unadjusted pH of the acid solution.

The data indicated that as the PO$_2$ increased, the selectivity to N-phosphonomethylglycine increased.

TABLE 4

Effect of Varying PO$_2$

| Example | psig (kPa) | Selectivity to N-phosphonomethyl glycine (Mole %) at the indicated time (h) | Yield of N-phosphonomethyl glycine (Mole %) at the indicated time (h) |
|---|---|---|---|
| 17 | 40 (210) | 56 (6) | 54 (6) |
| 18 | 70 (450) | 65 (6) | 63 (6) |
| 19 | 100 (690) | 68 (6) | 66 (6) |
| 20 | 130 (890) | 75 (6) | 73 (6) |
| 21 | 225 (1550) | 81 (2) | 7δ (2) |
| 22 | 450 (3100) | 83 (1½) | 81 (1½) |

Examples 23 through 29 and Control 1

Examples 23 through 29 and Control 1, shown in Table 5, illustrate the effect of varying the form of the manganese catalyst on selectivity to N-phosphonomethylglycine. The reaction temperature was 90° C., the PO$_2$ was 100 psig (700 kPa), the initial concentration of N-phosphonomethyliminodiacetic acid was 0.1M, the manganese concentration was 0.004M and the reaction time was 1 h. The pHi was the unadjusted pH of the acid solution.

The mN(III)chloro-(phthalocyaninato) (Control 1) was not catalytic.

TABLE 5

Effect of Varying Form of Manganese

| Example | Form | Selectivity to N-phosphonomethyl glycine (Mole %) at 1 h. | Selectivity at 6 h. |
|---|---|---|---|
| 23 | [1]Mn (II)/Mn (III) | 43 | 75 |
| 24 | Mn (II) acetate | 18 | 75 |
| 25 | Mn (III) acetate | 20 | 75 |
| 26 | Mn (II) sulfate | 16 | 75 |
| 27 | [2]Mn (II) (acac) | 20 | 75 |
| 28 | [3]MnCl$_2$ 4H$_2$O | 82 | — |
| 29 | [3]MnO$_2$ | 70 | 73 |
| Control 1 | [4]Mn (III) | 1 | <10 |

[1]Mn acetate, 50/50 mole ratio Mn(II)/Mn(III)
[2]Mn(II)bis(acetylacetonate)
[3]PO$_2$ = 450 psig (3100 kPa) at 80° C. and Mn concentration was 0.01 M.
[4]Mn(III)chloro-(phthalocyanato)

Examples 30 through 42

Examples 30 through 42, shown in Table 6, further illustrate the present invention. The initial pH, unless otherwise indicated, was the unadjusted pH at reaction temperature, the PO$_2$, unless otherwise indicated, is 100 psig (690 kPa), the initial concentration of N-phosphonomethyliminodiacetic acid was 0.1M, and the manganese catalyst was the mixture used in Example 1.

TABLE 6

| Example | Run Time (h) | Catalyst Concentration (M) | Temperature (°C.) | Yield (Mole %) | Conversion (Mole %) |
|---|---|---|---|---|---|
| 30 | 1 | .01 | 90 | 10 | 96 |
| 31 | 1 | .02 | 80 | 42 | 97 |
| 32 | 1[a] | .007 | 80 | 32 | 91 |
| 33 | 2 | .01 | 70 | 8 | 95 |
| 34 | 2 | .007 | 80 | 65 | 95 |
| 35 | 2[b] | .007 | 70 | 74 | 96 |
| 36 | 2[c] | .007 | 80 | 25 | 75 |
| 37 | 2[d] | .007 | 80 | 22 | 63 |
| 38 | 2 | .004 | 90 | 42 | 80 |
| 39 | 2 | .002 | 90 | 60 | 75 |

TABLE 6-continued

| Example | Run Time (h) | Catalyst Concentration (M) | Temperature (°C.) | Yield (Mole %) | Conversion (Mole %) |
|---|---|---|---|---|---|
| 40[e] | 2½ | .007 | 80 | 85 | 100 |
| 41[f] | 1 | .007 | 80 | 95 | 97 |
| 42[g] | 5 | .07 | 80 | 19 | 84 |

[a]pHi = 2.3
[b]PO$_2$ = 130 psig (810 kPa)
[c]PO$_2$ = 40 psig (275 kPa)
[d]pHi = 1.35
[e]PO$_2$ = 225 psig (1545 kPa)
[f]PO$_2$ = 450 psig (3100 kPa)
[g]Catalyst was Mn(II) acetylacetonate, the PO$_2$ was 450 psi (3000 kPa) and the initial concentration of N-phosphonomethyliminodiacetic acid was 0.5 M.

Examples 43 through 65

Examples 43 through 65, shown in Table 7, illustrate the use of cobalt catalysts in the present invention. The initial concentration of N-phosphonomethiminodiacetic acid was 0.1 M and the catalyst was Co(II)(SO$_4$). The pH was the unadjusted pH of the N-phosphonomethyliminodiacetic acid of the solution, unless otherwise indicated when it was adjusted with sodium hydroxide or sulfuric acid solution.

TABLE 7

| Example | Run Time (h) | Catalyst Concentration (M) | Temperature (°C.) | Yield (Mole %) | Conversion (Mole %) | pH | PO$_2$ (psi) |
|---|---|---|---|---|---|---|---|
| 43 | 5.5 | 0.02 | 80 | 73 | 100 | unadjusted | 450 |
| 44 | 3.0 | 0.02 | 85 | 85 | 100 | " | 450 |
| 45 | 1.75 | 0.02 | 90 | 75 | 100 | " | 450 |
| 46 | 5.5 | 0.02 | 85 | 90 | 100 | " | 450 |
| 47 | 5 | 0.02 | 85 | 98 | 100 | " | 1000 |
| 48 | 2.0[a] | 0.02 | 85 | 21 | 31 | " | 450 |
| 49 | 5.5 | 0.02 | 85 | 74 | 98 | " | 300 |
| 50 | 3.0[b] | 0.036 | 90 | 87 | 100 | " | 450 |
| 51 | 4.0[c] | 0.048 | 80 | 64 | 97 | " | 450 |
| 52 | 5.0[d] | 0.125 | 85 | 52 | 99 | " | 450 |
| 53 | 18[f] | 0.5 | 100 | 16 | 100 | 6.25 | 100 |
| 54 | 18[e] | 0.5 | 100 | 28 | 98 | 1.80 | 100 |
| 55 | 18[e] | 0.5 | 100 | 16 | 100 | 2.25 | 100 |
| 56 | 18[e] | 0.5 | 100 | 0 | 100 | 4.00 | 100 |
| 57 | 18[e] | 0.5 | 100 | 35 | 98 | 1.09 | 100 |
| 58 | 18[e] | 0.5 | 100 | 9.9 | 22 | 0.77 | 100 |
| 59 | 18[e] | 0.5 | 100 | 17 | 98 | 1.7 | 100 |
| 60 | 18[e] | 0 | 100 | 0 | 98 | 9.00 | 100 |
| 61 | 18[e] | 0.01 | 100 | 20 | 40 | 0.44 | 100 |
| 62 | 2[f] | 0.01 | 100 | 28 | 98 | 1.80 | 100 |
| 63 | 2[g] | 0.01 | 100 | 26 | 98 | 1.80 | 100 |
| 64 | 18[h] | 0.01 | 100 | 26 | 98 | 1.74 | 100 |
| 65 | 5[i] | 0.2 | 85 | 66 | 99 | 1.7 M | 450 |

[a]The catalyst was Co (III) (acetylactonate)$_3$.
[b]The initial N-phosphonomethyliminodiacetic acid concentration was 0.3 M.
[c]The initial N-phosphonomethyliminodiacetic acid concentration was 0.4 M.
[d]The initial N-phosphonomethyliminodiacetic acid concentration was 1.0 M.
[e]The initial N-phosphonomethyliminodiacetic acid concentration was 0.5 M, the catalyst was CoCl$_2$.
[f]The initial N-phosphonomethyliminodiacetic acid concentration was 0.5 M and the catalyst was Co(NO$_3$)$_2$.
[g]The initial N-phosphonomethyliminodiacetic acid concentration was 0.5 M and the catalyst was cobalt acetate.
[h]The initial N-phosphonomethyliminodiacetic acid concentration was 0.5 M and the catalyst was CoBr$_2$.
[i]The initial N-phosphonomethyliminodiacetic acid concentration was 0.4 M.

Examples 66 through 85

Examples 66 through 85, shown in Table 8, illustrate iron catalysts suitable for the present invention. The PO$_2$ was 100 psi (690 kPa), the catalyst concentration was 0.01 M, the reaction temperature was 100° C, the run time was 18 h, and the initial concentration of the N-phosphonomethyliminodiacetic acid was 0.5M, which formed a slurry. When NaBr was added, the concentration was also 0.01 M.

TABLE 8
Iron Catalysts

| Example | Catalyst | Yield (mole %) | Conversion (mole %) | pH |
|---|---|---|---|---|
| 66 | Fe(SO$_4$)$_2$ | 21 | 36 | 6.25 |
| 67 | Fe(SO$_4$)$_2$ | 18 | 28 | 10.0 |
| 68 | Fe(SO$_4$)$_2$ | 6 | 14 | 5.0 |
| 69 | Fe(SO$_4$)$_2$ + NaBr | 5 | 6 | 3.0 |
| 70 | Fe(SO$_4$)$_2$ + NaBr | 12 | 14 | 5.0 |
| 71 | Fe(SO$_4$)$_2$ + NaBr | 26 | 40 | 6.25 |
| 72 | Fe(SO$_4$)$_2$ + NaBr | 28 | 84 | 7.0 |
| 73 | Fe(SO$_4$)$_2$ + NaBr | 29 | 84 | 8.0 |
| 74 | Fe(SO$_4$)$_2$ + NaBr | 37 | 83 | 9.0 |
| 75 | iron (III) (dicyano) bis (o-phenanthroline) tetrafluoroborate salt | 6 | 12 | 6.25 |
| 76 | iron (III) (dicyano) bis (o-phenanthroline) tetrafluoroborate salt | 8 | 10 | 7.0 |
| 77 | iron (III) (dicyano) bis (o-phenanthroline) tetrafluoroborate salt | 3 | 12 | 9.0 |
| 78 | iron (III) (dicyano) bis (o-phenanthroline) tetrafluoroborate salt | 3 | 12 | 10.0 |
| 79 | K$_3$Fe(CN)$_6$[a] | 3 | 14 | 3.0 |
| 80 | " | 8 | 24 | 5.0 |
| 81 | " | 21 | 46 | 6.3 |
| 82 | " | 30 | 76 | 7.0 |
| 83 | " | 37 | 80 | 9.0 |
| 84 | " | 32 | 80 | 10.0 |
| 85 | Fe(SO$_4$)$_2$ + Al(NO$_3$)$_3$ | 21 | 72 | 6.0 |

[a]Run time is 8 h.

Examples 86 through 106 and Control 2

Examples 86 through 106 and Control 2, shown in Table 9, illustrate nickel, chromium, ruthenium, aluminum, and molybdenum catalysts appropriate for the present invention. The conditions are as for those given in Table 8. The catalyst for Control 2, CuCl$_2$, appeared to be ineffective.

TABLE 9

Nickel Chromium, Ruthenium, Aluminum and Molybdenum Catalysts

| Examples | Catalyst | Yield (mole %) | Conversion (mole %) | pH |
|---|---|---|---|---|
| 86 | NiBr$_2$ | 0.2 | 22 | 5.0 |
| 87 | " | 0.2 | 10 | 4.0 |
| 88 | " | 10 | 34 | 7.0 |
| 89 | " | 9 | 38 | 8.4 |
| 90 | " | 8 | 34 | 10.4 |
| 91 | CrCl$_3$ | 1 | 12 | 1.26 |
| 92 | " | 4 | 16 | 2.0 |
| 93 | " | 16 | 76 | 3.0 |
| 94 | " | 0.1 | 14 | 4.0 |
| 95 | " | 12 | 52 | 5.0 |
| 96 | " | 4 | 22 | 7.0 |
| 97 | " | 13 | 58 | 6.25 |
| 98 | RuBr$_3$ | 70 | 8 | 6.25 |
| 99 | " | 18 | 34 | 10.0 |
| 100 | RuBr$_2$(Me$_2$SO)$_4$ | 34 | 62 | 6.25 |
| 101 | " | 25 | 48 | 11.0 |
| 102 | Al(NO$_3$)$_3$ | 11 | 34 | 6.25 |
| 103 | Al(NO$_3$)$_3$ + NaCl | 12 | 16 | 6.25 |
| Control 2 | CuCl$_2$ | 0.2 | 14 | 6.25 |
| 104 | K$_4$Mo(CN)$_8$ | 4 | 22 | 4.0 |
| 105 | " | 32 | 48 | 6.0 |
| 106 | " | 10 | 30 | 9.0 |

Examples 107–109

Examples 107 through 109 shown in Table 10, illustrate vanadium catalysts suitable for the present invention. The reaction temperature was 70° C., the PO$_2$ was 100 psi (690 kPa), the initial concentration of N-phosphonomethyliminodiacetic acid was 0.5 M, the catalyst concentration was 0.033M.

TABLE 10

Vanadium Catalysts

| Examples | Catalyst | Run Time (h) | Yield (mole %) | Conversion (mole %) |
|---|---|---|---|---|
| 107 | VO(acetylacetonate)$_2$ | 2 | 40 | 67 |
| 108 | VOSO$_4$(hydrate) | 2.25 | 42 | 94 |
| 109 | VOSO$_4$(hydrate)$^a$ | 5 | 54 | 91 |

$^a$The initial concentration of N-phosphonomethyl-iminodiacetic acid was 0.15 M and the concentration of catalyst was 0.015 M.

Examples 110 and 111

Examples 110 and 111 shown in Table 11 illustrate cerium catalysts suitable for the present invention. The reaction temperature was 90° C. and the PO$_2$ was 130 psi (897 kPa).

TABLE 11

Cerium Catalysts

| Example | Catalyst | Run Time (h) | Catalyst Concentration (M) | N-phosphonomethyl-iminodiacetic acid Concentration (M) | Yield (mole %) | Conversion (mole %) |
|---|---|---|---|---|---|---|
| 110 | Ce(NH$_4$)$_4$(SO$_4$)$_4$ | 3 | 0.1 | 1.0 | 7 | 45 |
| 111 | Ce(NH$_4$)$_4$(SO$_4$)$_4$ | 3 | 0.01 | 0.1 | 30 | 80 |

We claim:

1. A process for the production of N-phosphonomethylglycine comprising contacting N-phosphonomethyliminodiacetic acid with a molecular oxygen-containing gas in the presence of an aqueous soluble catalyst selected from the group consisting of the salts and salt complexes of manganese.

2. The process of claim 1 wherein the catalyst is at least one of a manganese(II), a manganese(III), or a manganese(IV) salt.

3. The process of claim 1 wherein the catalyst is selcted from the group comprising manganese acetate, manganese sulfate, manganese(II)bis(acetylacetonate) and manganese cloride.

4. The process of claim 3 wherein the catalyst is a mixture of manganese(II) and manganese(III) salts.

5. The process of claim 4 wherein the salts are manganese acetate salts in a mole ratio in the range of 1:10 to 10:1.

6. A process for the production of N-phosphonomethylglycine comprising contacting N-phosphonomethyliminodiacetic acid with molecular oxygen in the presence of an aqueous soluble catalyst selected from the group consisting of the salts and salt complexes of manganese, wherein the reaction temperature is in the range of about 25° to 150° C., the reaction pressure is in the range of about atmospheric (101kPa) to about 3000 psig (20,700 kPa), the partial pressure of oxygen is in the range of about 1 psig (6.9 kPa) to about 3000 psig (20,700 kPa) and the initial pH is in the range of about 0.1 to 7.0.

7. The process of claim 1 wherein the N-phosphonomethyliminodiacetic acid is present as a slurry.

* * * * *